United States Patent [19]

Kasugai

[11] Patent Number: 4,605,617

[45] Date of Patent: Aug. 12, 1986

[54] PROCESS FOR CULTURING ANAEROBIC BACTERIA AND AGENTS FOR PREPARING CULTURE ATMOSPHERE

[75] Inventor: Makoto Kasugai, Tokyo, Japan

[73] Assignee: Mate, Inc., Tokyo, Japan

[21] Appl. No.: 691,370

[22] Filed: Jan. 14, 1985

Related U.S. Application Data

[63] Continuation of Ser. No. 424,328, Sep. 27, 1982, abandoned.

[30] Foreign Application Priority Data

Sep. 30, 1981 [JP] Japan .................. 56-153830

[51] Int. Cl.$^4$ .......... C12Q 1/02; C12N 1/20; C12M 1/34
[52] U.S. Cl. .................. 435/29; 435/253; 435/291; 422/61; 422/239; 422/305
[58] Field of Search ........ 435/243, 253, 313, 801, 435/287, 291, 294, 296, 299, 810, 29; 422/61, 239, 305

[56] References Cited

U.S. PATENT DOCUMENTS

| | | |
|---|---|---|
| 2,463,143 | 6/1947 | Brewer .................. 435/801 |
| 3,246,959 | 4/1966 | Brewer .................. 23/282 |
| 3,338,794 | 11/1964 | Bladel .................. 435/801 |
| 4,038,148 | 7/1977 | Miller et al. .................. 435/801 |
| 4,287,306 | 9/1981 | Brewer .................. 435/801 |

FOREIGN PATENT DOCUMENTS 2083496 3/1982 United Kingdom .............. 435/253

OTHER PUBLICATIONS

The Condensed Chemical Dictionary 8th ed., Hawley, p. 387.

Primary Examiner—Raymond N. Jones
Assistant Examiner—Marianne M. Cintins
Attorney, Agent, or Firm—Wegner & Bretschneider

[57] ABSTRACT

A process for culturing anaerobic bacteria in an atmosphere containing 10% carbon dioxide and no oxygen. An agent for producing such atmosphere comprises carbon dioxide-generating deoxidizer adapted to remove oxygen twice the volume of generated carbon dioxide.

6 Claims, 1 Drawing Figure

FIG
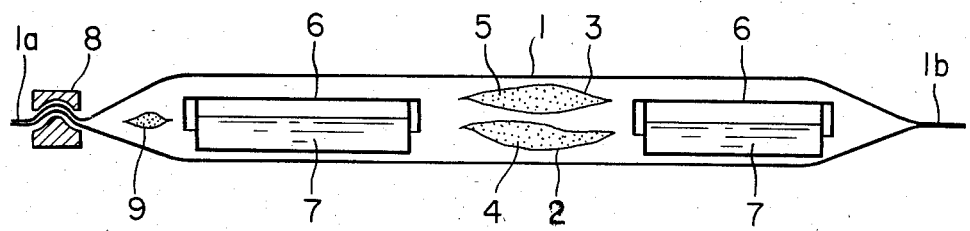

PROCESS FOR CULTURING ANAEROBIC BACTERIA AND AGENTS FOR PREPARING CULTURE ATMOSPHERE

This application is a continuation of U.S. application Ser. No. 424,328 filed Sept. 27, 1982, now abandoned.

FIELD OF THE INVENTION This invention relates to a process for culturing anaerobic, bacteria, particularly for preparing an anaerobic atmosphere of 10% by volume of carbon dioxide and agents therefor.

BACKGROUND

Anaerobic bacteria in the present invention encompass all kinds of bacteria which suffer any adverse reaction towards oxygen.

Different methods have been disclosed for detecting the anaerobic bacteria by cultivating the anaerobic bacteria and such cultivation has been known to be useful as means for detecting different kinds of bacteria. A simple method for preparing an adequate atmosphere for such cultivation is required, especially for clinical purposes. Various deoxidizers and carbon dioxide-generators have been developed, and various methods for preparing a culture atmosphere having a carbon dioxide content of 3-5% by volume have been put to practical use. However, the conventional methods still have various drawbacks. Namely, the number of the species of bacteria detectable by one cultivation test is limited, and the detecting test procedure is complicated.

It is too troublesome particularly in the clinical use to weigh out a specified amount of deoxidizers and carbon dioxide-generators according to the volume of each culture vessel since a great number of test samples must be cultured in the clinics depending upon daily needs. Thus there is much to be desired in the prior art.

OBJECTS OF THE INVENTION

It is a main object of the present invention to overcome the named drawbacks in the prior art.

It is an object of the present invention to provide a simpler process and agents for producing an anaerobic atmosphere enabling to detect as many as possible typical species of bacteria by one cultivation test.

It is another object of the present invention to provide a process and agents for preparing an anaerobic atmosphere containing 10% by volume of carbon dioxide simply by enclosing small packages of an atmosphere-adjusting agent in culture vessels.

SUMMARY OF THE INVENTION

According to the present invention, an atmosphere containing not exceeding 0.1% by volume of oxygen and 10±2% by volume of carbon dioxide is provided for culturing anaerobic bacteria. The present invention provides a process for preparing an anaerobic atmosphere by enclosing an agent enclosed in a gas-permeable inner bag, the inner bag being put in a sealed culture vessel, the agent being capable of deoxidizing, as well as generating carbon dioxide so adjusted as to produce such a relation that the volume of the removed oxygen is twice that of the generated carbon dioxide.

BRIEF DESCRIPTION OF DRAWING

The drawing of the single FIGURE is a longitudinal sectional view of an embodiment of an anaerobic cultivation device of the invention.

The drawing is presented to demonstrate a preferred embodiment for better illustration of the invention and not for limitation thereof. In the following preferred embodiments will be described in detail, which however should not be construed to limit the invention thereto. Any modifications and changes apparent to those in the art may be made within the gist of the invention as claimed.

DETAILED DESCRIPTION OF THE PREFERRED EMBODIMENTS

The present invention is based on the fact that most typical anaerobic bacteria are well cultured in an atmosphere not only free of oxygen but containing about 10% by volume of carbon dioxide.

It has been known in the art to use carbon dioxide-generators together with deoxidizers to regulate the carbon dioxide content to a level of 5% by volume. According to this manner, *Fusobacterium nucleatum* among eight typical species of the anaerobic bacteria has heretofor been impossible to be detected. However, when carbon dioxide is 10% by volume, *Fusobacterium nucleatum* can be also cultured and detected. Thus another cultivation test can be omitted for detecting all typical kinds of these bacteria. Further tests have proved that the process of the present invention realizes the detection of 30 typical kinds of bacteria including said 8 bacteria by culturing them. As a culture medium, fixed culture medium is suitable, however, other mediums are also applicable. Typical anaerobic bacteria which can be detected by the invention are as follows: Bacteroids, Fusobacterium, Clostridium, Propionibacterium, Lactobacillus, Peptococcus, Peptostreptococcus and Veillonella. Six of them except Clostridium and Lactobacillus are known to be particularly clinically important from the pathogenic view point.

It has been confirmed that the inventive process is applicable to 30 kinds of anaerobic bacteria including above 8 kinds, and further study in progress may reveal further application.

The cultivation proceeds in an atmosphere containing not more than 0.1% by volume (% refers to % by volume hereinafter) of oxygen and 10±2% of carbon dioxide during 24-48 hours at shortest after inoculation and preferably 6-48 hours. In this process, deoxidizing and carbon dioxide-generating agent according to the present invention provides an ideal atmosphere (of less than 0.1% oxygen with approximately 10% carbon dioxide) within about 3 hours. Other agents reacting more slowly may be used.

One type of the typical deoxidizing and carbon dioxide-generating agents according to the invention has the following composition:

(a) ascorbic acid and/or its salts
(b) carbonate(s) and/or hydrogen carbonate(s) of alkali, and
(c) accelerator(s)

Ascorbic acid encompasses both L-ascorbic acid and D-iso-ascorbic acid. The carbonates and hydrogen carbonates of alkali metal such as Na, Li, K and alkaline earth metal such as Mg, Ca etc. are suitable as the second component. Hydroxides of alkali metals and alkaline earth metals may be optionally added to the composition.

Some deliquescent salts such as calcium chloride may be also contained in the composition. As the accelerators, a mixture of ferrous salts and active carbon is most preferred, the amount of the accelerator being chosen according to the requisite reaction speed. Typical ferrous salts encompass ferrous sulfate, ferrous chloride, ferrous hydroxide, ferrous carbonate, and ferrous oxide, preferably hydrated ferrous sulfate. Powdered active carbon is conventionally produced by activating carbon with steam, $CO_2$, air, chloride or vacuum heating or according to other known manners.

Some examples of the basic composition of each agent are shown as follows:

| (A) | parts by weight | |
|---|---|---|
|  | (A-1) | (A-2) |
| L-ascorbic acid | 14 | 14 |
| active carbon | 14 | 12 |
| $FeSO_4.7H_2O$ | 30–50 | 58 |
| $CaCl_2.2H_2O$ | 0 | 6 |
| $Ca(OH)_2$ | 0 | 3 |
| $NaHCO_3$ | 7 | 6 |
| $Na_2CO_3.10H_2O$ | 7 | 6 |

Another example using powdery iron as a deoxidizer has following composition:

| (B) | parts by weight |
|---|---|
| powdery iron | 10 |
| $FeSO_4.7H_2O$ | 56 |
| $Ca(OH)_2$ | 10 |
| $Na_2SO_3.7H_2O$ | 7 |
| $NaHCO_3$ | 10 |
| $CaCl_2.2H_2O$ | 7 |
| active carbon | 1.5 |

The compositions hereinabove mentioned remove or absorb oxygen simultaneously generating carbon dioxide to maintain the carbon dioxide content at 10% in the culture atmosphere during 24–48 hours after sealing. In the practical use, additional deoxidizers or carbon dioxide-generators can be used in combination of said compositions according to the conditions of temperature, moisture etc. In such a case every components have to be decreased in the amounts according to additional components, provided that removed oxygen is twice the volume of the generated carbon dioxide.

As long as this principle is maintained, any kinds of variation are allowed. So, the composition may be composed of a combination of two groups of agents as follows: One of them being a group of the deoxidizing agent incapable of generating carbon dioxide, the other being a group with both capable of generating carbon dioxide and removing oxygen; provided that, e.g., the volume of generated carbon dioxide of the latter group is equivalent to the oxygen removed (or absorbed) and, at the same time, the speed of removing oxygen with the former group be approximately the same as that of the latter. Analogously, various combinations of the components are possible in correspondance to the difference of the reaction speed in case of the components having various reaction rates, i.e., different ratios between deoxidizing speed and carbon dioxide-generating speed.

As the deoxidizers some iron compounds are also well known. Japanese patent Kokoku publication Nos. 54(1979)-438, 54(1979)-439, 54(1979)-471, 54(1979)-472, 54(1979)-476 etc disclose various ferrous deoxidizers. Those are applicable in this invention. The partinent disclosures as disclosed in the above JP Kokoku publications are herewith incorporated in this Specification. A combination of ascorbic acid or its salts/alkali hydroxide/accelerators is also a useful deoxidizer. This composition includes alkali hydroxides (Calcium hydroxide is preferable) instead of alkali carbonates and alkali hydrogen carbonates in the compositions (hereinbefore mentioned) of the carbon dioxide-generating deoxidizers. In this case, as a composition of carbon dioxide-generating deoxidizer, it is possible to employ such a composition that generates carbon dioxide equivalent to the volume of removed oxygen. To this end, e.g., following composition is useful.

|  | parts by weight |
|---|---|
| sodium-L-ascorbate | 6 |
| $NaHCO_3$ | 6 |
| $Na_2CO_3.10H_2O$ | 6 |
| $FeSO_4.7H_2O$ | 2 |
| active carbon | 6 |

There are two types of the carbon dioxide generators. One is a carbonate such as sodium hydrogen carbonate, sodium carbonate, potassium carbonate, sodium sesquicarbonate and the like. The other is acidic compounds capable of generating carbon dioxide on dissolving in water resulting in a weak acidic pH (pH<6) such as ascorbic acid, tartaric acid, succinic acid, malic acid, fumaric acid, lactic acid etc, preferably ascorbic acid.

When the net-volume of the culture vessels is known, a further variation of the process is possible. Namely, it is possible to apply a combination of a deoxidizer removing oxygen up to 10% of the net volume of the culture vessel with a carbon dioxide-generating deoxidizer generating the same volume of carbon dioxide as the oxygen removed.

A significant merit of the agents of the invention resides in that it is unnecessary to weigh out many sorts of components with different ratios according to each culture vessel. All that the users have to do is to enclose the composition of an amount not less than the minimum amount for removing all oxygen of the vessels in the vessels. Therefore, the inventive process is significantly convenient on use.

It is more convenient to sealingly package the agents in a bag with double layers. The bag consists of an outer bag made of gas-impermeable plastic film and an inner bag made of gas-permeable sheet, e.g., plastic film, paper or cloth. For the purpose of long storage, additional covering with an aluminium foil or a laminated plastics-metal foil is also useful.

On use, the outer bag is cut open, then the inner bag is enclosed in a culture vessel which may be a large gas-impermeable bag or envelope.

Another merit of the invention resides in that the process requires no special vessel having pressure resistance such as vacuum vessel as is conventional in the prior art. The cultivation proceeds in a gas-impermeable envelope under the condition of a slightly reduced pressure of 10% $CO_2$ in place of 21% $O_2$. The gas-impermeable envelope may be conventional one. The same envelope for storing the agents before use may be used as the culture vessel. Using the agents of the invention, when all the oxygen amounted to 21% of the air is removed, carbon dioxide of its half volume is consequently generated. Thus the content of carbon dioxide theoretically results in 11.7% at the final stage. In this process the carbon dioxide content practically provides a range of 10±2%. The anaerobic cultivation can be performed at the content of 10% carbon dioxide promptly as occasion demands and in each culture vessel of a desired volume as well as individually. Through a transparent envelope employed as the culture vessel, every specimen can be observed without opening the envelope sealed for culturing.

The test results according to the inventive process are shown as follows:

[Test 1]

A prescribed amount of the ascorbate composition of carbon dioxide-generating deoxidizers hereinbefore mentioned as (A) was enclosed in a sealed culture vessel of 250 ml. Both contents of oxygen and carbon dioxide were measured and found 10.2% carbon dioxide with oxygen of less than 0.1% after 24 hours, and 10.4% carbon dioxide with oxygen of less than 0.1% after 48 hours.

[Test 2]

Each one package of the deoxidizers sold by Mitsubishi Gas Chemical Co., Ltd. with the commercial name of "Ageless S-50" and "Ageless S-30", and 2 packages of the carbon dioxide-generating deoxidizer sold by Toppan Printing Co., Ltd. with the commercial name of "C-500" were enclosed in the culture vessel of a net volume of 250 ml. After 3 hours at 37° C., 9.8% carbon dioxide and less than 0.1% oxygen were confirmed. From 24 hours to 48 hours after enclosure, an anaerobic atmosphere (less than 0.1% oxygen) was maintained and the carbon dioxide content varied from 10.1% to 9.2%.

[Test 3]

In an analogous manner with Test 2, various volumes of culture vessels ranging from 200 to 500 ml were tested exhibiting similar results. Judging from these test results, this process quickly accomplishes the anaerobic condition and maintains approximately 10% $CO_2$ content during a period of time sufficient for the anaerobic culture regardless of the vessel volume when sufficient amount of the agent is applied.

A further simple embodiment will be hereinbelow disclosed with reference to a drawing. An outer envelope 1 is made of a transparent and gas-impermeable film with the oxygen-permeability of less than 50 cc/m².atm.dry and preferably less than 20 cc/m².atm.dry. The film encompasses, e.g., nylon, polypropylene- or polyester-film each coated with polyvinylidene chloride, polyvinylidene film, copolymer film of vinyl alcohol with ethylene and the like. One end of the envelope is sealed. A petri dish 6 after innoculation of a specimen on a culture medium 7 is enclosed in the outer envelope 1. Then the permeable inner bags 2, 3 containing the compositions of carbon dioxide-generating deoxidizers 4, 5 are also enclosed in the envelope together with a known indicator 9 for the detection of anaerobic condition in color. Then, the open side 1a is sealed with a clip 8. One or two, or any more pieces of the inner bags 2, 3 (2 pieces being shown in the drawing) may be used as needed. Other known methods for sealing or gas-tightly closing like heat sealing etc. are applicable for sealing the open end of the envelope.

About 10% of carbon dioxide is generated at the anaerobic stage, hence the envelope 1 is not intensely crushed and the conventional petri dishes can resist well against the pressure. Thus special pressure vessels are not required. Every petri dish can be observed from the outside and the examiner can individually check the growth of colony from one dish to another dish at any time without opening the transparent envelope. Control of the temperature is easy because of small size and the thin layer of the envelope made of the gas-impermeable film contrary to that of the conventional pressure vessel or vaccum vessel.

Besides, as the reactions in this process are neither endothermic nor exothermic, the temperature remains steady without special care as well as easily controllable at need. Usually, the moisture is not aspired, nor expired by the reaction according to the preferred embodiment.

[Example 1]

As a carbon dioxide-generating deoxidizer the composition A-1 hereinabove mentioned was used to maintain the atmosphere of 10±2% carbon dioxide and less than 0.1% oxygen during 6–48 hours after inoculation on the GAM agar culture medium. Following strains were cultured for 48 hours at 37° C., and the growth of these strains were observed and compared with respect to the size of the colony: Bacteroides, Fusobacterium, Clostridium, Propionibacterium, Lactobacillus, Peptococcus, Peptostreptococcus and Veillonella. All of them grew up each to form a sufficiently large colony and detected. In the same manner another 30 kinds of anaerobic strain were tested and detected successfully.

[Comparative Test 1]

Cultivation was carried out in an atmosphere of 5% carbon dioxide otherwise in the similar manner to Example 1. Fusobacterium could not be detected.

[Comparative Test 2]

Cultivation was performed at a content of 20% carbon dioxide with less than 0.1% oxygen. Most strains could not be detected because of their poor growth. Accordingly, those tests as disclosed show the atmosphere containing 10% carbon dioxide can effectively work for detecting more strains which are contained in the specimens clinically sampled. Thus the process of the present invention has turned out useful particularly in the field of clinical culture testing.

What is claimed is:

1. A process for detecting a plurality of types of anaerobic bacteria by culturing test samples in a closed culture vessel, comprising;
    introducing into the culture vessel an inoculated culture meduim and an agent comprising a composition which removes oxygen and generates carbon dioxide such that the volume of removed oxygen is approximately twice as great as the volume of carbon dioxide generated;
    closing the vessel; and
    maintaining the interior atmosphere in the culture vessel in a state where the oxygen concentration does not exceed 0.1% by volume and the carbon dioxide concentration is between 10% and 12% by volume for the period of at least 3 to 24 hours after closing the vessel.

2. A process as claimed in claim 1, where the maintaining step is continued for up to 48 hours after closing the vessel.

3. A process as defined in claim 1, wherein said closed culture vessel is an oxygen-impermeable and transparent bag with its open end being gas-tightly closed or sealed.

4. An agent for preparing an anaerobic culture atmosphere with a carbon dioxide concentration between 10% and 12% by volume for the period of at least 3 to 24 hours for detecting anaerobic bacteria of a plurality of types, comprising a composition consisting essentially of a deoxidizer and a carbon dioxide-generation deoxidizer having approximately the same deoxidizing speed as said deoxidizer, the carbon dioxide-generating deoxidizer which removes oxygen and generates carbon dioxide at approximately the same volumetric rate, said deoxidizer and said carbon dioxide-generating deoxidizer being separately contained in oxygen-impermeable inner bags, both being contained in an oxygen impermeable outer bag before use, said deoxidizer comprising powdery iron, and said carbon dioxide-generating deoxidizer comprising;
   at least one of ascorbic acid, and ascorbic acid salt, or a mixture thereof;
   an alkali hydroxide; and
   an accelerator.

5. An agent as defined in claim 4, wherein the carbon dioxide-generating deoxidizer comprises:
   (a) ascorbic acid, ascorbic salt or a mixture thereof,
   (b) carbonate or hydrogen carbonate of alkali, or a mixture thereof, and
   (c) reaction accelerator.

6. An agent as defined in claim 4, wherein said carbon dioxide-generating deoxidizer comprises:
   (a) powdery iron,
   (b) ferrous sulfate, and
   (c) carbonate or hydrogen carbonate of alkali, or a mixture thereof.

* * * * *